United States Patent [19]

Zhou et al.

[11] Patent Number: 5,198,209
[45] Date of Patent: Mar. 30, 1993

[54] CONDITIONING SHAMPOO

[75] Inventors: Jingshi Zhou, Kentwood; David J. Fochtman, Comstock Park, both of Mich.

[73] Assignee: Amway Corporation, Ada, Mich.

[21] Appl. No.: 833,991

[22] Filed: Feb. 11, 1992

[51] Int. Cl.$^5$ .............................................. A61K 7/11
[52] U.S. Cl. ........................................ 424/71; 424/70
[58] Field of Search .................... 252/8.8; 424/70, 71

[56] References Cited

U.S. PATENT DOCUMENTS

| | | | |
|---|---|---|---|
| 2,826,551 | 3/1958 | Geen | 252/89 |
| 3,208,911 | 9/1965 | Oppliger | 167/87 |
| 3,950,510 | 4/1976 | Adams | 424/70 |
| 3,964,500 | 6/1976 | Drakoff | 132/70 |
| 4,185,087 | 1/1980 | Morlino | 424/70 |
| 4,364,837 | 12/1982 | Pader | 252/173 |
| 4,374,825 | 2/1983 | Bolich, Jr. et al. | 424/70 |
| 4,416,793 | 11/1983 | Barrat et al. | 252/8.8 |
| 4,425,364 | 1/1984 | Vanlerberghe et al. | 424/358 |
| 4,490,356 | 12/1984 | Sebag et al. | 424/70 X |
| 4,563,347 | 1/1986 | Starch | 424/70 |
| 4,639,321 | 1/1987 | Barrat et al. | 252/117 |
| 4,704,272 | 11/1987 | Oh et al. | 424/70 X |
| 4,728,457 | 3/1988 | Fieler et al. | 252/174.15 |
| 4,741,855 | 5/1988 | Grote et al. | 252/142 |
| 4,775,527 | 10/1988 | Bires et al. | 424/70 X |
| 4,777,037 | 10/1988 | Wagman et al. | 424/70 X |
| 4,788,006 | 11/1988 | Bolich, Jr. et al. | 424/70 |
| 4,793,994 | 12/1988 | Helioff et al. | 424/70 X |
| 4,842,850 | 6/1989 | Vu | 424/70 |
| 4,902,499 | 2/1990 | Bolish, Jr. et al. | 424/70 |
| 4,906,459 | 3/1990 | Cobb et al. | 424/70 |
| 4,933,176 | 6/1990 | van Reeth | 424/70 |
| 4,954,335 | 9/1990 | Janchipraponvej | 424/70 |
| 4,976,956 | 12/1990 | Noe | 424/70 |
| 5,034,218 | 7/1991 | Duvel | 424/70 |

OTHER PUBLICATIONS

Helioff, Michael W. et al., "Shampoo Innovation Via a New Surfactant," *D&CI*, Apr. 1988, pp. 38.42.

*Primary Examiner*—Thurman K. Page
*Attorney, Agent, or Firm*—Price, Heneveld, Cooper, DeWitt & Litton

[57] ABSTRACT

The present invention relates to an improved conditioning shampoo composition which is stable, thoroughly cleanses the hair, and imparts improved physical and cosmetic properties to hair such as wet and dry comb, wet and dry feel, gloss, static control and manageability, yet does not cause build-up on human hair as is common with many conditioning shampoos. The shampoo composition comprises by weight 8%–20% of an anionic surfactant, 0.1%–5% of a water soluble cationic surfactant, 0.1%–8% of an insoluble, dispersed or emulsified, non-volatile silicone, and 0.5%–5% of a suspending or emulsifying nonionic surfactant such as an N-alkylated-2-pyrrolidone having a structure:

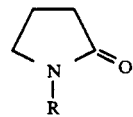

(III)

wherein R is an alkyl moiety, straight chain or branched chain, including from about 8 to about 16 carbon atoms, and water. Preferred embodiments additonally may contain from about 0.5% to about 1% by weight of a non-volatile amine-functional siloxane.

20 Claims, No Drawings

CONDITIONING SHAMPOO

BACKGROUND OF THE INVENTION

This invention relates to a new composition for washing and conditioning hair and, more particularly, to a new composition providing both a shampooing and a conditioning action in a single application.

Human hair becomes soiled due to sebum secreted naturally by the scalp as well as soil and other atmospheric contaminants which accumulate on the hair. The build-up of sebum causes the hair to have a greasy, dirty feel, poor manageability, and an unattractive appearance. Shampooing the hair cleans by removing from the hair excess oil, sebum, atmospheric contaminants, and the residues due to the usage of a variety of hair styling products, such as sprays, gels and mousses. The most effective shampoos are those that contain high lather synthetic anionic surfactants, such as the long chain alkyl sulfates and the long chain alkyl ether sulfates. These shampoos are very effective for cleansing the hair but, after rinsing with water, they leave the hair in an unmanageable state. Thoroughly cleansed hair is extremely difficult to comb in both wet and dry states because the individual hair fibers tend to tangle with each other. Also, thoroughly cleansed hair in the dry state has undesirable electrostatic properties in a relatively low humidity atmosphere which cause the hair to "fly away," thereby further reducing the overall manageability of the hair.

A variety of means have been developed to alleviate the problems associated with after-shampooed hair. These range from using after-shampoo hair conditioner to including hair conditioning agents directly to the shampoo compositions. After-shampoo hair conditioners are easily formulated but must be applied in a separate step following the shampooing. This, of course, is time-consuming and inconvenient. Among the most effective hair conditioners are those that contain cationic surfactants such as long chain dialkyl dimonium chlorides.

The formulation of shampoo with conditioning agents has been difficult due to several reasons. One problem relates to the usual incompatibility between anionic surfactants and cationic surfactants. The combination of anionic surfactants with cationic surfactants often reduces the respective cleansing and conditioning effectiveness of each surfactant. This is because combining a cationic surfactant with an anionic surfactant causes the formation of a water insoluble species. A partial solution to this incompatibility problem in formulating conditioning shampoos is to examine other surfactants such as nonionics and amphoterics for use as conditioning agents in place of cationics. Unfortunately, the use of these other surfactants has not solved all the problems associated with formulating conditioning shampoos.

Another problem associated with formulating a conditioning shampoo is the instability that results when water-insoluble conditioning agents are included in the composition, such as the non-volatile silicones which have a good conditioning property that provides a degree of softness and luster to the hair. A particularly difficult problem to solve with silicone-containing conditioning shampoos is that of keeping a dispersed, water-insoluble, non-volatile silicone material suspended in stable form while retaining the desirable performance of the conditioning shampoos. The following references represent efforts by industry to solve this problem: U.S. Pat. No. 5,034,218 to Duvel, U.S. Pat. No. 4,704,272 to Oh et al.; and U.S. Pat. No. 4,902,499 to Bolish, Jr. et al. Despite these efforts, there is a continuing need for the discovery of improved stable conditioning shampoos which have compatible anionic surfactants and cationic conditioning surfactants, thoroughly cleanse the hair, and impart improved physical and cosmetic properties to hair such as wet and dry comb, wet and dry feel, gloss, static control and manageability, yet do not cause build-up on human hair as is common with many conditioning shampoos.

SUMMARY OF THE INVENTION

The present invention provides a stable, conditioning shampoo that cleanses the human hair and, at the same time, provides improved physical and cosmetic properties to the human hair in a single application. The shampoo composition comprises 8%-20% of an anionic surfactant, 0.1%-5% of a water soluble cationic surfactant, 0 1%-8% of an insoluble, dispersed or emulsified, non-volatile silicone, 0.5%-5% of a suspending or emulsifying nonionic surfactant such as an N-alkylated-2-pyrrolidone having a structure:

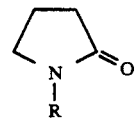

wherein R is an alkyl moiety, straight chain or branched chain, including from about 8 to about 16 carbon atoms; and water. All percentages are by weight unless otherwise stated.

DETAILED DESCRIPTION OF THE PREFERRED EMBODIMENT

The conditioning shampoo composition of the preferred embodiment includes the following ingredients in the ranges, preferred ranges and best modes indicated:

TABLE 1

| Ingredients | Range | Preferred Range | Best Mode |
|---|---|---|---|
| Anionic Surfactants | 8-20% | 10-18% | 14-18% |
| Nonvolatile Silicone | 0.1-8% | 1-4% | 1.5-2.5% |
| Cationic Surfactants | 0.1-5% | 0.5-3% | 0.5-1.5% |
| N-alkylated-2-pyrrolidones | 0.5-5% | 1-3% | 1.5-2.5% |
| Miscellaneous Ingredients | 0.5-10% | 0.5-5% | same |
| Water - Balance to | 100% | same | same |

A. Synthetic Anionic Surfactants

An essential component of the present compositions is the synthetic anionic surfactant which is present in the preferred embodiment at a level from about 8% to about 20% by weight, preferably from about 10% to about 18%. Synthetic anionic surfactants useful in this embodiment include long chain alkyl sulfates and long chain alkyl ether sulfates. These surfactants have good cleansing properties. These surfactants have the respective formulas $ROSO_3M$ and $RO(C_2H_4O)_xSO_3M$ wherein R is an alkyl or alkenyl of about 10 to about 20 carbon atoms, x is 1 to 10, and M is a water-soluble cation such as ammonium, sodium, potassium, lithium or triethanolamine.

Exemplary anionic surfactants that are useful in the composition and method of the preferred embodiment include, but are not limited to, the ammonium, monoethanolamine, diethanolamine, triethanolamine, isopropylamine, sodium, potassium, lithium or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amine; or combinations thereof. A preferably useful anionic surfactant is a mixture of a lauryl sulfate and a lauryl ether sulfate.

Other suitable anionic surfactants include, but are not limited to, compounds in the classes known as alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates and isothienates; or combinations thereof.

B. Water-insoluble, Non-volatile Silicone

The composition of the preferred embodiment includes from about 0.1% to about 8% by weight, and preferably from about 1.0% to about 4% by weight of a water-insoluble, non-volatile silicone compound. The dispersed silicone particles should not be soluble either in water or in the shampoo matrix. Among the preferred silicone compounds are polyalkyl siloxanes and polyalkylaryl siloxanes because they have good conditioning properties.

The non-volatile polyalkyl siloxanes which may be used include, for example, polydimethyl siloxanes with viscosities ranging from about 5 to about 1,000,000 centistokes at 25° C. These siloxanes are commercially available from the General Electric Company as the Viscasil series and from Dow Corning Chemical Company as the Dow Corning 200 series. Preferably, the viscosity ranges from about 1,000 centistokes to about 600,000 centistokes.

The non-volatile polyalkylaryl siloxanes which may be used include, for example, polymethylphenylsiloxanes having viscosities of about 15 to about 65 centistokes at 25° C. These siloxanes are commercially available from the General Electric Company as SF1075 methyl phenyl fluid or from Dow Corning Chemical Company as Dow Corning 556 Cosmetic Grade Fluid.

If a low viscosity polyalkyl siloxane is used, for example, polydimethylsiloxane having a viscosity of about 25 centistokes at 25° C., the desired amount of conditioning may not be fully achieved. While polyalkyl siloxane compounds of a viscosity of up to 1,000,000 centistokes at 25° C. do provide conditioning benefits to hair, it is preferred that about 1.5-2.5% of a polyalkyl siloxane compound of a viscosity of about 30,000 to 100,000 centistokes at 25° C. be used in the formulation.

In a particularly preferred embodiment, the composition also includes from about 0.1% to about 2% by weight, and preferably from about 0.5% to about 1% by weight of a water-insoluble, non-volatile amine-functional siloxane in addition to the polyalkyl siloxanes and polyalkylaryl siloxanes included in the composition. A preferred amine-functional silicone for use is trimethylsilylamodimethicone which has a viscosity from about 50 to about 500 centistokes at 25° C. This siloxane is commercially available from the General Electric Company as SF1705 or from Dow Corning Chemical Company as Dow Corning Q2-8220, or from Dow Corning Chemical Company as Dow Corning 929 Emulsion.

The data shown in Table 2 illustrate the superior conditioning benefits to hair which are achieved when an amine functional silicone is used with the polydimethyl siloxane. Note the improved hair tress evaluation results in Formula B where both sources of silicone are used, particularly the surprising boost in antistatic effect. It is preferred that a 1.0% level of Trimethylsilylamodimethicone be used.

TABLE 2

| | Formula A | Formula B |
|---|---|---|
| CTFA Name | | |
| Purified water | 31.65 | 30.65 |
| Hydroxypropyl methyl cellulose | 0.60 | 0.60 |
| Ammonium lauryl sulfate (28%) | 45.00 | 45.00 |
| Ammonium laureth sulfate (28%) | 10.00 | 10.00 |
| Disodium lauryl sulfosuccinate (30%) | 3.00 | 3.00 |
| Isostearamidopropyl morpholine lactate (25%) | 4.00 | 4.00 |
| Lauryl pyrrolidone | 2.00 | 2.00 |
| Dimethicone | 2.00 | 2.00 |
| Trimethylsilylamodimethicone | 0.00 | 1.00 |
| Color, fragrance, preservative qs. to | 100.00 | 100.00 |
| Hair Tress Evaluation Results: | | |
| Test Parameter (1 worst, 9 best) | | |
| Wet comb | 6.0 | 7.6 |
| Wet feel | 6.0 | 7.0 |
| Dry comb | 7.4 | 8.2 |
| Dry feel | 6.8 | 7.8 |
| Static control | 2.0 | 3.8 |

C. Water-soluble Cationic Surfactant Conditioners

The composition of the preferred embodiment also includes from about 0.1% to about 5% by weight, and preferably from about 0.5% to about 3% by weight of a water-soluble cationic surfactant, preferably an acid-neutralized amidoamine compound. These acid-neutralized amidoamine compounds are compatible with anionic surfactants and provide conditioning properties not seen in other formulations incorporating amidoamines specifically at these levels. The preferred amidoamine compounds have a general structural formula (I) or (II):

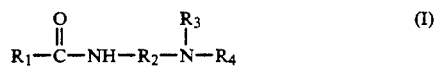

(I)

$$R_1-\overset{O}{\overset{\|}{C}}-NH-R_2-\overset{R_3}{\overset{|}{N}}-R_4$$

(II)

$$R_1-\overset{O}{\overset{\|}{C}}-NH-R_2-Y$$

where $R_1$ is a fatty acid chain containing from about 11 to about 21 carbon atoms, $R_2$ is an alkyl group containing from about two to about four carbon atoms, $R_3$ is hydrogen, methyl, ethyl or a hydroxyalkylene group containing from about one to about three carbon atoms, $R_4$ is methyl, ethyl or a hydroxyalkylene group containing from about one to about three carbon atoms, and Y is a heterocyclic nitrogen-containing moiety, like morpholine.

An example of an amidoamine compound having the general structural formula (I) that can be used in the composition and method of the preferred embodiment is the compound named stearamidoethylethanolamine according to CTFA Dictionary. Among the other suitable amidoamine compounds which can be used is stearamidoethyldiethanolamine. In addition, suitable amidoamine compounds include compounds having either one or two hydroxymethyl, hydroxypropyl, methyl or ethyl moieties, or combinations thereof, present on an amino nitrogen in place of the hydroxyethyl moieties. Examples of such amidoamine compounds include, but are not limited to, dimethylaminopropyl stearamide, diethylaminoethyl stearamide, and dimethylaminopropyl myristamide.

An example of an amidoamine compound having the general structural formula (II) that can be used in the composition and method of the preferred embodiment is the compound named isostearamidopropylmorpholine according to CTFA Dictionary. Other suitable amidoamine compounds include stearamidopropylmorpholine.

After neutralization with a suitable acid, the above-described amidoamine compounds exhibit the properties of a cationic surfactant. In the free-amine state, the amidoamine compounds are insoluble in water. After acid neutralization, however, the amidoamine compounds are water soluble. Consequently, in the acid-neutralized state, the acid-neutralized amidoamine compounds behave like a cationic surfactant, are substantive to human hair and impart improved conditioning properties to human hair.

The acid used to neutralize the amidoamine compound can be any acid of sufficient strength to neutralize a free-amine nitrogen. Such acids include, but are not limited to, hydrochloric acid, sulfuric acid, nitric acid, phosphoric acid, lactic acid, citric acid, tartaric acid, acetic acid, gluconic acid, glycolic acid and propionic acid, or combinations thereof.

There are some commercially available acid pre-neutralized amidoamine compounds, such as isostearamidopropyl morpholine lactate under the trade name INCROMATE ISML from Croda Inc. and stearamidopropyl dimethylamine lactate under the trade name INCROMATE SDL from Croda Inc.

To achieve the full advantage of the preferred embodiment, the amidoamine compound is pre-neutralized with lactic acid. In general, the pH of the final composition is within a range of from about 4 to about 7, and more preferably in a pH range of from about 5 to about 6.5.

The data shown in Table 3 below illustrate the conditioning benefits to the hair obtained by the addition of a pre-neutralized amidoamine cationic surfactant to a shampoo composition at the specific levels of the preferred embodiment, especially in the areas of wet comb, dry comb and dry feel.

TABLE 3

| CTFA Name | Formula C | Formula B |
|---|---|---|
| Purified water | 34.65 | 30.65 |
| Hydroxypropyl methyl cellulose | 0.60 | 0.60 |
| Ammonium lauryl sulfate (28%) | 45.00 | 45.00 |
| Ammonium laureth sulfate (28%) | 10.00 | 10.00 |
| Disodium lauryl sulfosuccinate (30%) | 3.00 | 3.00 |
| Isostearamidopropyl morpholine lactate (25%) | 0.00 | 4.00 |
| Lauryl pyrrolidone | 2.00 | 2.00 |
| Dimethicone | 2.00 | 2.00 |
| Trimethylsilylamodimethicone | 1.00 | 1.00 |
| Color, fragrance, preservative qs. to | 100.00 | 100.00 |
| Hair Tress Evaluation Results: | | |
| Test Parameter (1 worst, 9 best) | | |
| Wet comb | 6.2 | 7.2 |
| Wet feel | 6.0 | 6.8 |
| Dry comb | 6.8 | 7.8 |
| Dry feel | 7.4 | 7.8 |

TABLE 3-continued

| | Formula C | Formula B |
|---|---|---|
| Static control | 3.0 | 3.0 |

D. Pyrrolidone Nonionic Surfactant to Suspend or Emulsify Silicone

Another essential component of the present compositions of this embodiment is a suspending or emulsifying agent. The nonionic surfactants known as the N-alkylated-2-pyrrolidones of general structure (III) wherein R is an alkyl moiety, straight chain or branched chain, including from about 8 to about 16 carbon atoms effectively suspend or emulsify silicone and provide unexpected stability to the silicone containing composition.

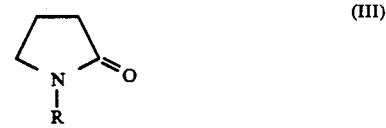

(III)

Specific N-alkylated-2-pyrrolidones found useful in the composition of the preferred embodiment include lauryl pyrrolidone, available commercially under the trade name SURFADONE LP-300 from International Specialty Product.

The importance of the presence of the N-alkylated-2-pyrrolidones in the present formulation is shown by the data in Table 4 which illustrate that conditioning shampoo compositions using nonionic surfactants such as glycol distearate and stermamide MEA separate a short period of time after their formulation.

TABLE 4

| CTFA Name | Formula D | Formula E |
|---|---|---|
| Purified water | 32.15 | 32.15 |
| Hydroxypropyl methyl cellulose | 0.60 | 0.60 |
| Ammonium lauryl sulfate (28%) | 45.00 | 45.00 |
| Ammonium laureth sulfate (28%) | 10.00 | 10.00 |
| Disodium lauryl sulfosuccinate (30%) | 3.00 | 3.00 |
| Isostearamidopropyl morpholine lactate (25%) | 3.00 | 3.00 |
| Glycol distearate | 2.00 | 0.00 |
| Steramide MEA | 0.00 | 2.00 |
| Dimethicone | 2.00 | 2.00 |
| Trimethylsilylamodimethicone | 0.50 | 0.50 |
| Color, fragrance, preservative qs. to | 100.00 | 100.00 |

Formula D separated at day 10 when stored at 50° C. while Formula E separated at day 7 when stored at 50° C. Sample data shown in Tables 5, 6 and 7 list a variety of possible combinations of the essential and preferred ingredients. Note that all the proposed combinations but one, Sample 10, maintained their stability over a period of at least 28 days at a temperature of 50° C. Like Formulas D and E above, Sample 10 did not incorporate an N-alkylated-2-pyrrolidone in the formulation. It is preferred that the N-alkylated-2-pyrrolidones be present in the formulation at a level of from about 0.5% to about 5% by weight. It is particularly preferable that they be present at a level of from about 1% to about 3% by weight.

E. Water

Water is the last essential component of the preferred embodiment and forms the remainder of the composition. It is generally present at a level of from 20% to about 90% by weight, preferably from about 50% to about 80% by weight.

F. Optional Ingredients

The conditioning shampoos herein can contain a variety of nonessential optional ingredients suitable for making such compositions acceptable. Such conventional optional ingredients are well-known to those skilled in the art of this field, e.g., preservatives such as benzyl alcohol, methylparaben, propylparaben, imidazolidinyl urea, quaternium-15, chloromethyl isothiazolinone and methyl isothiazolinone, phenoxyethanol, and DMDM hydantoin. Pearlescent agents such as ethylene glycol stearate, ethylene glycol distearate, mica coated by titanium dioxide can also be included. Among the suggested thickeners and viscosity modifiers which can be used are a diethanolamide of a long chain fatty acid (e.g., Cocamide MEA, Lauramide DEA), amine oxides, fatty alcohols such as cetearyl alcohol, sodium chloride, ammonium chloride, sodium sulfate, synthetic cellulose gums (e.g., hydroxypropylmethylcellulose, hydroxyethylcellulose), synthetic polymers (e.g., Carbomers), and ethyl alcohol.

The pH of the composition can be adjusted by agents such as monosodium phosphate and disodium phosphate, citric acid, succinic acid, phosphoric acid, sodium hydroxide, sodium carbonate, etc. Other optional ingredients include hydrolyzed animal and vegetable proteins, and their derivatives; quaternary compounds such as cetyl trimethyl ammonium chloride, stearyldimethyl benzyl ammonium chloride, and quaternium-22; perfumes; dyes; sequestering agents such as disodium ethylenediamine tetraacetate; antioxidants such as tocopherol, BHT, and BHA; and UV absorbers such as benzophenones. Such optional ingredients generally are used individually at a level of from about 0.0% to about 10% by weight, preferably from about 0.05% to about 5.0% by weight. Overall, the optional ingredients are used in the composition at a level of from about 0.5% to about 10% by weight, and preferably from about 0.5% to about 5% by weight.

G. Method of Manufacture

The compositions of the preferred embodiment can be made by a single phase addition procedure. Referring to the composition of Sample 1 in Table 5, water is added to the mixing tank and heated to 175° F.-185° F. Hydroxypropylmethylcellulose is then added to the water. The entire amount of ammonium laureth sulfate is then added to the mixture along with a similar amount of ammonium lauryl sulfate. During addition, it is important that the temperature of the mixture is maintained at 160° F.-165° F. The isostearmidopropyl morpholine lactate is added and mixed well until the mixture is clear. Disodium lauryl sulfosuccinate is then thoroughly mixed into the combination. The glycol stearate is added until dissolved followed by the addition of lauryl pyrrolidone which may cause the viscosity of the mixture to increase. At this point, the agitation speed is increased and the dimethicone is slowly added to the mixture. The mixture is then mixed under high agitation for 30 to 60 minutes.

Following the long mixing, trimethylsilylamodimethicone is mixed well into the composition and the mixture is removed from heat. The remaining ammonium lauryl sulfate is then added. At the temperature below 125° F., all miscellaneous optional ingredients are added with good agitation. The mixture is then agitated until reaching room temperature. Upon completion, the viscosity range of the composition is from about 5,000 centistokes to about 25,000 centistokes at 25° C.

The performance of formulas 16 and 19 were compared to a commercially available conditioning shampoo acting as the control. The commercially available conditioning shampoo contained the following ingredients:

water, ammonium lauryl sulfate, ammonium laureth sulfate, dimethicone, glycol distearate, ammonium xylenesulfonate, fragrance, cocamide MEA, tricetylmonium chloride, xanthan gum, cetyl alcohol, stearyl alcohol, sodium chloride, methylchloroisothiazolinone, methylisothiazolinone, sodium citrate, citric acid, D&C green No. 8, D&C yellow No. 10, and FD&C blue No. 1.

The type of test and the results are listed below:

A. CONSUMER IN-USE PANEL STUDY

Sample 19 vs. Control

Number of panelists: 20
Duration of the study: two weeks. One week of test Sample 19; one week of control.
Comparison parameters: overall acceptability; flash foaming; quality of the lather; lasting power of the lather; easy to rinse off; wet comb; wet feel; dry comb; dry feel; static control; gloss; and body/manageability.
Results: Sample 19 performed as well as the control. There is no significant difference between these two formulas in any of the parameter being tested. Sample 19 rated equal or higher numerically in the following parameters: easy to rinse off; wet comb; wet feel; dry comb; static control; and body/manageability.

B. TRESS EVALUATION

Sample 16 vs. Control

Number of experts evaluating hair tress: 5
Evaluation parameters: wet comb; wet feel; dry comb; dry feel; and static control.
Results: Sample 16 performed significantly better than the Control. Five experts are all in favor of Sample 16 in the following parameters: wet comb and wet feel. Four out of five experts favor Sample 16 over Control in the following parameters: dry comb; dry feel and static control.

C. SALON HALF HEAD STUDY

Sample 16 vs. Control

Number of subjects involved: 2
Number of experts evaluating the performance: 5
Comparison parameters: wet comb; wet feel; dry comb; dry feel; static control; gloss.
Results: Sample 16 performed as well as Control. There is no significant difference between the two formulas on the parameters being tested.

TABLE 5

| | SAMPLES | | | | | | |
| --- | --- | --- | --- | --- | --- | --- | --- |
| | 1 | 2 | 3 | 4 | 5 | 6 | 7 |
| Water | 30.50 | 30.75 | 32.14 | 41.80 | 42.80 | 38.35 | 37.10 |

TABLE 5-continued

| | SAMPLES | | | | | | |
|---|---|---|---|---|---|---|---|
| | 1 | 2 | 3 | 4 | 5 | 6 | 7 |
| Hydroxypropyl methylcellulose | 0.60 | 0.60 | 0.60 | 0.80 | 0.80 | 0.80 | 0.60 |
| Ammonium lauryl sulfate (28% active) | 45.00 | 45.00 | 45.00 | 35.00 | 35.00 | 35.00 | 42.00 |
| Ammonium laureth sulfate (28% active) | 10.00 | 10.00 | 10.00 | 15.00 | 15.00 | 15.00 | 12.00 |
| Disodium lauryl sulfosuccinate (30% active) | 3.00 | 3.00 | 3.00 | 0.00 | 0.00 | 0.00 | 0.00 |
| Glycol stearate | 1.80 | 0.00 | 0.00 | 0.00 | 0.00 | 2.00 | 1.80 |
| Lauryl pyrrolidone | 2.00 | 2.00 | 2.00 | 1.50 | 1.50 | 1.00 | 2.00 |
| Isostearmidopropyl morphine lactate (25% active) | 3.00 | 3.00 | 3.00 | 1.00 | 1.00 | 1.50 | 0.00 |
| Stearmidopropyl dimethylamine lactate (25% active) | 0.00 | 0.00 | 0.00 | 0.00 | 0.00 | 0.00 | 1.00 |
| Dimethicone | 2.00 | 2.00 | 2.00 | 1.50 | 1.50 | 2.50 | 2.00 |
| Trimethylsilylamodimeth | .50 | .50 | .50 | 0.00 | 0.00 | 0.00 | 0.00 |
| Miscellaneous Optional Ingredients | 2.10 | 3.65 | 2.26 | 3.40 | 2.40 | 3.85 | 1.50 |
| Total | 100.00 | 100.00 | 100.00 | 100.00 | 100.00 | 100.00 | 100.00 |
| Stability (28 days, 50° C.) | yes | yes | yes | yes | yes | yes | yes |

TABLE 6

| | SAMPLES | | | | | |
|---|---|---|---|---|---|---|
| | 8 | 9 | 10 | 11 | 12 | 13 |
| Water | 39.30 | 40.30 | 40.80 | 41.80 | 42.80 | 32.00 |
| Hydroxypropyl methylcellulose | 0.00 | 0.40 | 0.80 | 0.80 | 0.80 | 0.60 |
| Ammonium lauryl sulfate (28% active) | 35.00 | 35.00 | 35.00 | 35.00 | 35.00 | 45.00 |
| Ammonium laureth sulfate (28% active) | 15.00 | 15.00 | 15.00 | 15.00 | 15.00 | 10.00 |
| Disodium lauryl sulfosuccinate (30% active) | 0.00 | 0.00 | 0.00 | 0.00 | 0.00 | 3.00 |
| Glycol stearate | 0.80 | 0.00 | 0.00 | 0.00 | 0.00 | 0.00 |
| Lauryl pyrrolidone | 1.50 | 1.50 | 0.00 | 1.50 | 1.50 | 2.00 |
| Isostearmidopropyl morphine lactate (25% active) | 2.00 | 2.00 | 2.00 | 1.00 | 1.00 | 3.00 |
| Stearmidopropyl dimethylamine lactate (25% active) | 0.00 | 0.00 | 0.00 | 0.00 | 0.00 | 0.00 |
| Dimethicone | 2.50 | 1.00 | 2.50 | 1.50 | 1.50 | 2.00 |
| Dimethicone (12,500 cps) | 0.00 | 1.00 | 0.00 | 0.00 | 0.00 | 0.00 |
| Trimethylsilylamodimeth | 0.00 | 0.00 | 0.00 | 0.00 | 0.00 | 0.50 |
| Miscellaneous Optional Ingredients | 3.90 | 3.80 | 3.90 | 3.40 | 2.40 | 2.90 |
| Total | 100.00 | 100.00 | 100.00 | 100.00 | 100.00 | 100.00 |
| Stability (1 month, 50° C.) | yes | yes | no | yes | yes | yes |

TABLE 7

| | SAMPLES | | | | | |
|---|---|---|---|---|---|---|
| | 14 | 15 | 16 | 17 | 18 | 19 |
| Water | 39.80 | 39.30 | 33.10 | 38.80 | 31.65 | 38.35 |
| Hydroxypropyl methylcellulose | 0.80 | 0.50 | 0.60 | 0.80 | 0.60 | 0.80 |
| Ammonium lauryl sulfate (28% active) | 35.00 | 35.00 | 42.00 | 35.00 | 45.00 | 35.00 |
| Ammonium laureth sulfate (28% active) | 15.00 | 15.00 | 12.00 | 15.00 | 10.00 | 15.00 |
| Disodium lauryl sulfosuccinate (30% active) | 0.00 | 0.00 | 2.50 | 0.00 | 3.00 | 0.00 |
| Glycol stearate | 0.00 | 1.00 | 1.50 | 1.50 | 0.00 | 2.00 |
| Lauryl pyrrolidone | 1.50 | 1.30 | 1.50 | 1.00 | 2.00 | 1.00 |
| Isostearmidopropyl morphine lactate (25% active) | 2.00 | 2.00 | 2.00 | 2.00 | 3.00 | 1.50 |
| Dimethicone | 2.50 | 2.50 | 2.50 | 2.50 | 2.00 | 2.50 |
| Trimethylsilylamodimeth | 0.00 | 0.00 | 0.60 | 0.00 | 1.00 | 0.00 |
| Miscellaneous Optional Ingredients | 3.40 | 3.40 | 1.70 | 3.40 | 1.75 | 3.85 |
| Total | 100.00 | 100.00 | 100.00 | 100.00 | 100.00 | 100.00 |
| Stability (28 days, 50° C.) | yes | yes | yes | yes | yes | yes |

The embodiments of the invention in which an exclusive property or privilege is claimed are defined as follows:

1. A stable conditioning shampoo composition comprising by weight:

A. From about 8% to about 20% anionic surfactant;

B. From about 0.1% to about 5% cationic surfactant;
C. From about 0.1% to about 8% insoluble, non-volatile silicone;
D. From about 0.5% to about 5% of an N-alkylated-2-pyrrolidone having a structure:

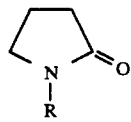
(III)

wherein R is an alkyl moiety, straight chain or branched chain, including from about 8 to about 16 carbon atoms; and E. Sufficient water to 100%.

2. A shampoo composition as claimed in claim 1, wherein the N-alkylated-2-pyrrolidone is from about 1% to about 3% by weight.

3. A shampoo composition as claimed in claim 2, wherein the N-alkylated-2-pyrrolidone is lauryl pyrrolidone.

4. A shampoo composition as claimed in claim 1, wherein the anionic surfactant is from about 10% to about 18% by weight.

5. A shampoo composition as claimed in claim 4, wherein said anionic surfactant is a long chain alkyl sulfate having the formula $ROSO_3M$ wherein R is an alkyl or alkenyl of about 10 to about 20 carbon atoms and M is a water-soluble cation.

6. A shampoo composition as claimed in claim 5, wherein said anionic surfactant comprises 12-15% ammonium lauryl sulfate.

7. A shampoo composition as claimed in claim 4, wherein said anionic surfactant is a long chain alkyl ether sulfate having the formula $RO(C_2H_4O)_xSO_3M$ wherein R is an alkyl or alkenyl of about 10 to about 20 carbon atoms, x is 1 to 10, and M is a water-soluble cation.

8. A shampoo composition as claimed in claim 7, wherein said anionic surfactant comprises 2-5% ammonium lauryl ether sulfate.

9. A shampoo composition as claimed in claim 1, wherein the cationic surfactant is from about 0.5% to about 3% by weight.

10. A shampoo composition as claimed in claim 9, wherein said cationic surfactant is an acid-neutralized amidoamine wherein the amidoamine compounds have a general structural formula (I):

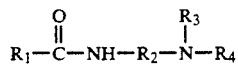
(I)

wherein $R_1$ is a fatty acid chain containing from about 11 to about 21 carbon atoms, $R_2$ is an alkyl group containing from about two to about four carbon atoms, $R_3$ is hydrogen, methyl, ethyl or a hydroxyalkylene group containing from about one to about three carbon atoms, and $R_4$ is methyl, ethyl or a hydroxyalkylene group containing from about one to about three carbon atoms.

11. A shampoo composition as claimed in claim 10, wherein said amidoamine is stearamidoethylethanolamine, stearamidoethyldiethanolamine, dimethylaminopropyl stearamide, diethylaminopropyl stearamide and dimethylaminopropyl myristamide.

12. A shampoo composition as claimed in claim 11, wherein said amidoamine compound is neutralized to a pH of from about 4 to about 7.

13. A shampoo composition as claimed in claim 12, wherein said amidoamine compound is neutralized to a pH of from about 5 to about 6.5.

14. A shampoo composition as claimed in claim 13, wherein said amidoamine compound is pre-neutralized with lactic acid.

15. A shampoo composition as claimed in claim 9, wherein said cationic surfactant is an acid-neutralized amidoamine where the amidoamine compounds have a general structural formula (II):

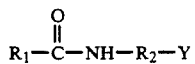
(II)

wherein $R_1$ is a fatty acid chain containing from about 11 to about 21 carbon atoms, $R_2$ is an alkyl group containing from about two to about four carbon atoms, and Y is a heterocyclic nitrogen-containing moiety, like morpholine.

16. A shampoo composition as claimed in claim 15, wherein said amidoamine is isostearamidopropylmorpholine and stearamidopropylmorpholine.

17. A shampoo composition as claimed in claim 1, wherein the non-volatile silicone is from about 1% to about 4% by weight.

18. A shampoo composition as claimed in claim 17, wherein said non-volatile silicone is selected from the group consisting of polyalkyl siloxanes and polyalkylaryl siloxanes.

19. A shampoo composition as claimed in claim 1, further comprising of from about 0.5% to about 1% by weight of a non-volatile amine-functional siloxane.

20. A shampoo composition as claimed in claim 19, wherein said amine-functional siloxane is trimethylsilylamodimethicone.

* * * * *

UNITED STATES PATENT AND TRADEMARK OFFICE
CERTIFICATE OF CORRECTION

PATENT NO. : 5,198,209

DATED : March 30, 1993

INVENTOR(S) : Jingshi Zhou et al.

It is certified that error appears in the above-identified patent and that said Letters Patent is hereby corrected as shown below:

Column 1, line 36:
    "b" should be --be--.

Column 3, line 36:
    "commercialy" should be --commercially--.

Column 7, line 37:
    "0.0%" should be --0.01%.

Signed and Sealed this

Twenty-second Day of March, 1994

Attest:

BRUCE LEHMAN

Attesting Officer     Commissioner of Patents and Trademarks